(12) United States Patent
Hsu et al.

(10) Patent No.: US 8,753,571 B2
(45) Date of Patent: Jun. 17, 2014

(54) SYSTEM AND METHOD FOR SANITIZING TOUCH SCREEN OF ELECTRONIC DEVICES

(75) Inventors: Cheng-Ta Hsu, New Taipei (TW); Cho-Hao Wang, New Taipei (TW)

(73) Assignee: Hon Hai Precision Industry Co., Ltd., New Taipei (TW)

( * ) Notice: Subject to any disclaimer, the term of this patent is extended or adjusted under 35 U.S.C. 154(b) by 283 days.

(21) Appl. No.: 13/246,870

(22) Filed: Sep. 28, 2011

(65) Prior Publication Data

US 2012/0268394 A1  Oct. 25, 2012

(30) Foreign Application Priority Data

Apr. 19, 2011  (TW) .............................. 100113469 A

(51) Int. Cl.
| | | |
|---|---|---|
| G05B 1/00 | (2006.01) | |
| A47L 11/00 | (2006.01) | |
| A47L 5/00 | (2006.01) | |
| B08B 3/00 | (2006.01) | |
| B08B 7/04 | (2006.01) | |
| A61L 2/00 | (2006.01) | |
| B05D 1/00 | (2006.01) | |
| B05D 1/02 | (2006.01) | |
| B05D 1/32 | (2006.01) | |
| B05D 1/40 | (2006.01) | |

(52) U.S. Cl.
CPC ... *A61L 2/00* (2013.01); *B08B 3/00* (2013.01); *B05D 1/00* (2013.01); *B05D 1/02* (2013.01); *B05D 1/322* (2013.01); *B05D 1/40* (2013.01)
USPC ................ 422/28; 422/3; 422/105; 422/119; 15/3; 15/319; 15/49.1; 15/363; 134/117; 134/118; 134/44; 134/84

(58) Field of Classification Search
CPC .............. A61L 2/00; B08B 3/00; B08B 1/28; B05D 1/00; B05D 1/02; B05D 1/322; B05D 1/40
USPC ............. 422/3, 28, 105, 119; 15/319, 3, 49.1, 15/363, 322; 134/117, 18, 44, 56 R, 84
See application file for complete search history.

(56) References Cited

U.S. PATENT DOCUMENTS

2009/0084409 A1*  4/2009  Okura et al. .................... 134/21

* cited by examiner

*Primary Examiner* — Monzer R Chorbaji
(74) *Attorney, Agent, or Firm* — Novak Druce Connolly Bove + Quigg LLP

(57) ABSTRACT

In a method for sanitizing a touch screen of an electronic device, the electronic device includes a first motor roller and a second motor roller and a screen sanitization system. The first motor roller connects to the second motor roller through a flexible pipe that is filled with a sanitizer. The first motor roller is scrolled to clean and sanitize a first protective film using sanitizer when the first protective film is overlaid on the surface of the touch screen, and a second protective film is drawn to overlay on the surface of the touch screen. The second motor roller is scrolled to clean and sanitize the second protective film using the sanitizer when the second protective film is overlaid on the surface of the touch screen, and the first protective film is drawn to overlay on the surface of the touch screen.

18 Claims, 4 Drawing Sheets

SYSTEM AND METHOD FOR SANITIZING TOUCH SCREEN OF ELECTRONIC DEVICES

BACKGROUND

1. Technical Field

The embodiments of the present disclosure relate to sanitization apparatuses and methods using electronic devices, and more particularly to a system and method for sanitizing a touch screen of an electronic device.

2. Description of Related Art

Touch screens have become more and more popular as input sources for computers and other electronic devices, such as an automatic teller machine (ATM) or an automatic ticketing machine. A touch is sensed by a touch screen of an electronic device when a finger or a stylus comes into contact with the surface of the touch screen. Most touch screens require direct contact with the skin of the finger of a user, and public touch panels such as ATMs are touched by many different users. However, these touch screens may provide a suitable home for bacteria, fungi, and other organisms which thrive and propagate based on the availability of moisture, temperature, and nutrients of the receptive surfaces. Thus, these microorganisms can pose serious health risks to users ranging from minor skin irritation to more serious toxic response and disease when the users touch the touch screen of the electronic device.

Known methods for keeping touch screens clean and sanitized include manually wiping the touch screens with a liquid antiseptic solution. However, this can only be done periodically and is not a long-lasting solution since the liquid will evaporate. Therefore, there is a need for a system and method for sanitizing touch screens to effectively eliminate the microorganisms from the electronic device.

DETAILED DESCRIPTION

The present disclosure, including the accompanying drawings, is illustrated by way of examples and not by way of limitation. It should be noted that references to "an" or "one" embodiment in this disclosure are not necessarily to the same embodiment, and such references mean at least one.

Figure 1:
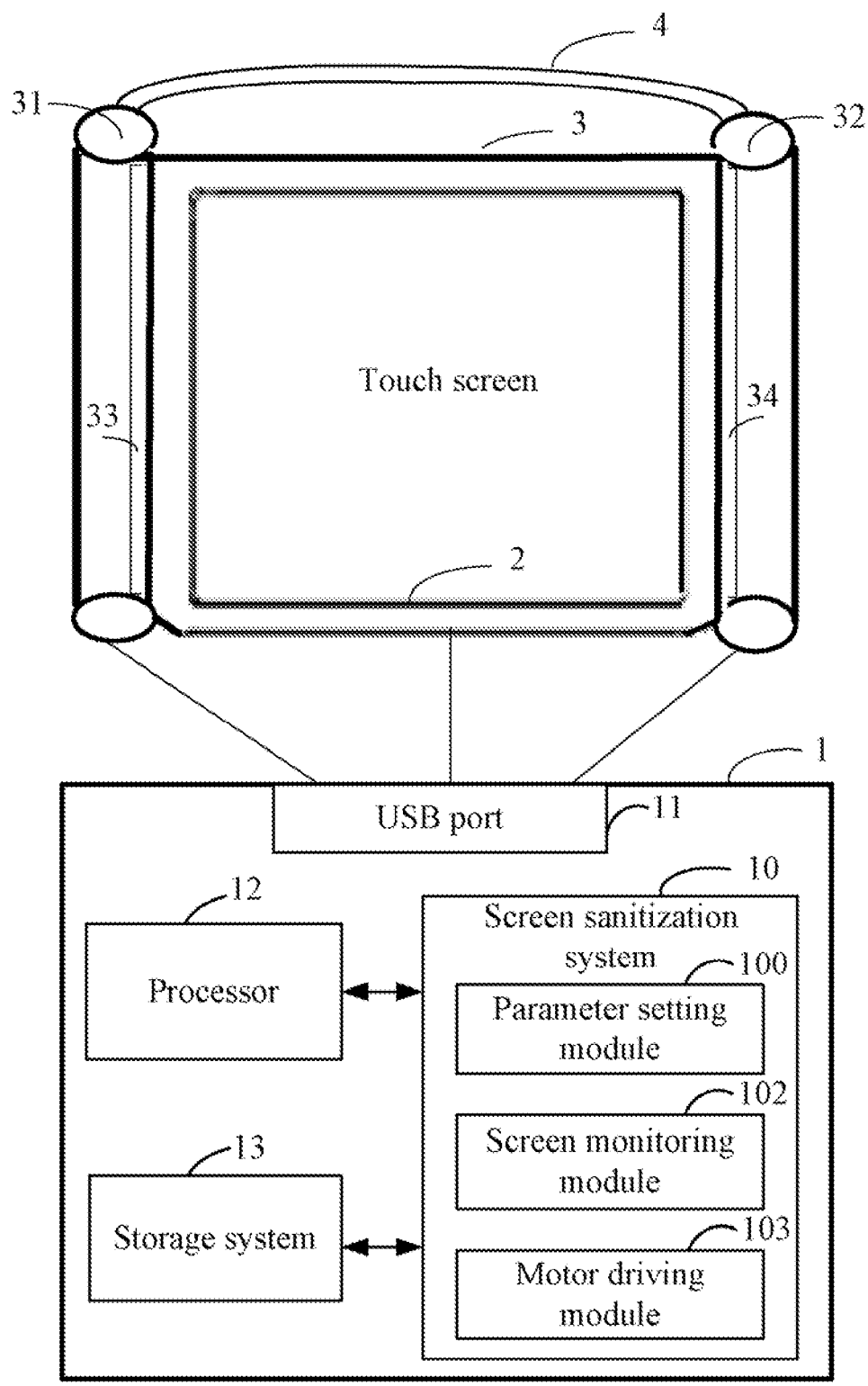
FIG. 1 is a block diagram of one embodiment of an electronic device including a screen sanitization system.

FIG. 1 is a block diagram of one embodiment of an electronic device 1 including a screen sanitization system 10. In the embodiment, the electronic device 1 may further include a touch screen 2, a universal serial bus (USB) port 11, at least one processor 12, and a storage system 13. The electronic device 1 may be an automatic teller machine (ATM) or an automatic ticketing machine, for example. The electronic device 1 processes a touch operation sensed by the touch screen 2 when a finger or a stylus contacts the surface of the touch screen 2. It should be understood that FIG. 1 illustrates only one example of the electronic device 1 that may include more or fewer components than illustrated, or a different configuration of the various components in other embodiments.

In one embodiment, the screen sanitization system 10 includes computerized instructions in the form of one or more programs that are executed by the at least one processor 12 and stored in the storage system 13. In one embodiment, the storage system 13 may be an internal storage system, such as a random access memory (RAM) for the temporary storage of information, and/or a read only memory (ROM) for the permanent storage of information. In some embodiments, the storage system 13 may also be an external storage system, such as an external hard disk, a storage card, or a data storage medium.

Figure 3:
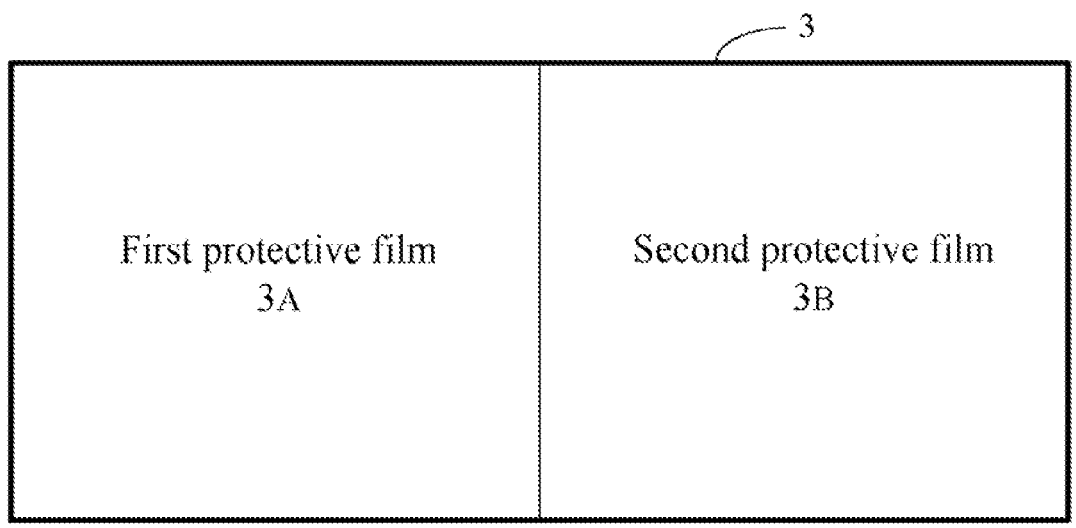
FIG. 3 is schematic diagram illustrating an example of a protective film overlaid on the surface of the touch screen.

In one embodiment, at least one protective film 3 is overlaid on the surface of the touch screen 2. The protective film 3 is a transparent film using a crystalline material without stickiness, and may be divided into a first protective film 3A and a second protective film 3B (see FIG. 3). In the embodiment, the length and width of the first protective film 3A and the second protection screen 3B are about the same as the length and width of the touch screen 2 respectively.

In the embodiment, a first motor roller 31 is positioned on the left side of the touch screen 2, and a second motor roller 32 is positioned on the right side of the touch screen 2. The first motor roller 31 includes a first clasp 33 that is used to clasp on the left edge of the first protective film 3A. The second motor roller 32 includes a second clasp 34 that is used to clasp on the right edge of the second protective film 3B. The first motor roller 31 connects to the second motor roller 32 through a flexible pipe 4 that is filled with a sanitizer (e.g., an alcohol type liquid). The first motor roller 31 and the second motor roller 32 electronically connects to the USB port 11 respectively.

Figure 4A:
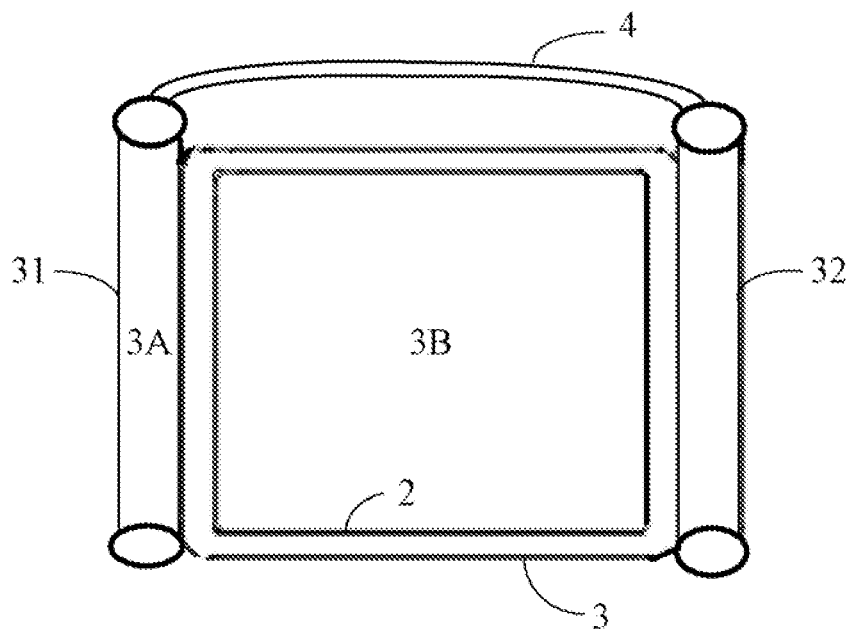
FIG. 4A and FIG. 4B are schematic diagrams illustrating an example of sanitizing the protective film overlaid on the surface of the touch screen.
Figure 4B:
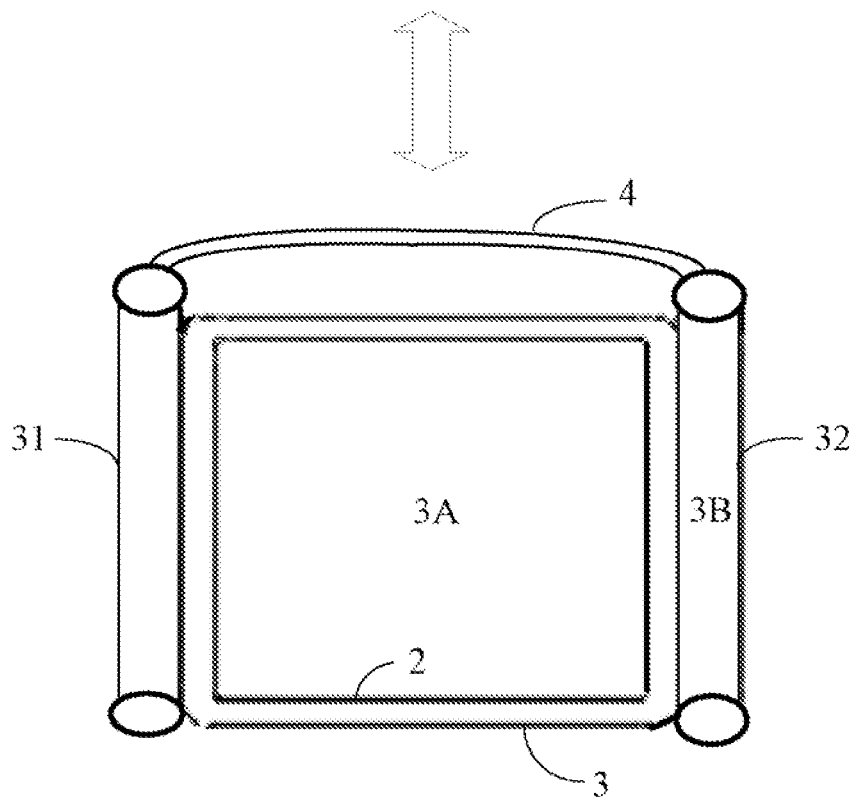

Referring to FIG. 4A, when the first motor roller 31 is scrolled, the first protective film 3A is drawn into the first motor roller 31 and is sanitized by the first motor roller 31 using the sanitizer of the flexible pipe 4, and then the second protective film 3B is overlaid on the surface of the touch screen 2. Referring to FIG. 4B, when the second motor roller 32 is scrolled, the second protective film 3B is drawn into the second motor roller 32 and is sanitized by the second motor roller 32 using the sanitizer of the flexible pipe 4, and then the first protective film 3A is overlaid on the surface of the touch screen 2.

In one embodiment, the screen sanitization system 10 includes a parameter setting module 100, a screen monitoring module 101, a motor driving module 102. The modules 100-102 may comprise computerized code in the form of one or more programs that are stored in the storage system 13 and executed by the processor 12 to provide functions for implementing the modules. In general, the word "module," as used herein, refers to logic embodied in hardware or firmware, or to a collection of software instructions, written in a programming language. In one embodiment, the program language may be Java, C, or assembly. One or more software instructions in the modules may be embedded in firmware, such as in an EPROM. The modules described herein may be implemented as either software and/or hardware modules and may be stored in any type of non-transitory computer-readable medium or other storage device. Some non-limiting examples of non-transitory computer-readable media include CDs, DVDs, flash memory, and hard disk drives.

The parameter setting module 100 is operable to set a time interval that determines how long and/or how often the touch screen 2 needs to be sanitized, and store the time interval into the storage system 13. In the embodiment, the time interval may be set according to the requirements of the user, for example, the time interval may be set as 10 minutes or 30 minutes.

The screen monitoring module 101 is operable to monitor a current state of the electronic device 1. The current state includes a working state of the electronic device 1 and an idle state of the electronic device 1. When the electronic device 1 is in the idle state, the screen monitoring module 101 counts a time using a timer of the electronic device 1, and determines whether the counted time is equal to the time interval. If the counted time is equal to the time interval, the screen monitoring module 101 detects whether the first protective film 3A or the second protective film 3B is overlaid on the surface of the touch screen 2.

The motor driving module 102 is operable to drive the first motor roller 31 to move along the surface of the first protective film 3A and sanitize the first protective film 3A using the sanitizer of the flexible pipe 4, and drive the second motor roller 32 to draw the second protective film 3B to be overlaid on the surface of the touch screen 2. Referring to 4A, the first protective film 3A may be cleaned and sanitized by the sanitizer when the first motor roller 31 is scrolled, and the second protective film 3B is overlaid on the surface of the touch screen 2.

The motor driving module 102 is further operable to drive the second motor roller 32 to move along the surface of the second protective film 3B and sanitize the second protective film 3B using the sanitizer of the flexible pipe 4, and drive the first motor roller 31 to draw the first protective film 3A to overlay on the surface of the touch screen 2. Referring to 4B, the second protective film 3B may be cleaned and sanitized by the sanitizer when the second motor roller 32 is scrolled, and the first protective film 3A is overlaid on the surface of the touch screen 2.

Figure 2:
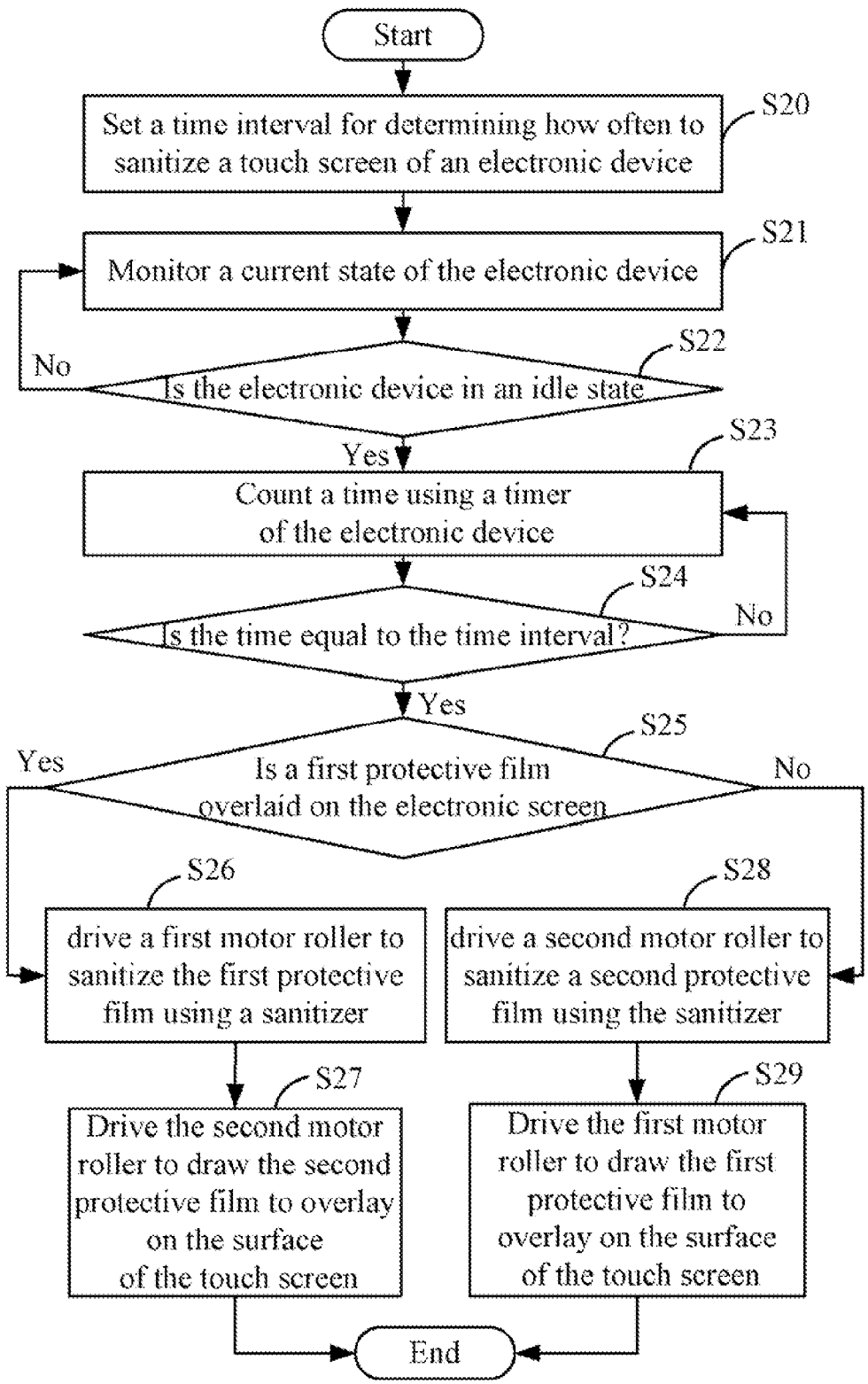
FIG. 2 is a flowchart of one embodiment of a method for sanitizing the touch screen of the electronic device of FIG. 1.

FIG. 2 is a flowchart of one embodiment of a method for sanitizing a touch screen, such as the touch screen 2 of the electronic device 1 of FIG. 1. Depending on the embodiment, additional blocks may be added, others removed, and the ordering of the blocks may be changed.

In block S20, the parameter setting module 100 sets a time interval that determines how long and/or how often the touch screen 2 needs to be sanitized, and stores the time interval into the storage system 13. In the embodiment, the time interval may be set according to the requirements of the user, for example, the time interval may be set as 10 minutes or 30 minutes.

In block S21, the screen monitoring module 101 monitors a current state of the electronic device 1 timely. In block S22, the screen monitoring module 101 determines whether the current state of the electronic device 1 is a working state or an idle state. If the current state of the electronic device 1 is the working state, block S22 is repeated. Otherwise, if the current state of the electronic device 1 is the idle state, block S23 is implemented.

In block S23, the screen monitoring module 101 counts a time using a timer of the electronic device 1. In block S24, the screen monitoring module 101 determines whether the counted time is equal to the time interval. If the counted time is not equal to the time interval, block S23 is repeated. Otherwise, if the counted time is equal to the time interval, block S25 is implemented.

In block S25, the screen monitoring module 101 detects whether the first protective film 3A or the second protective film 3B is overlaid on the surface of the touch screen 2. If the first protective film 3A is overlaid on the surface of the touch screen 2, block S26 is implemented. If the second protective film 3B is overlaid on the surface of the touch screen 2, block S28 is implemented.

In block S26, the motor driving module 102 drives the first motor roller 31 to move along the surface of the first protective film 3A and sanitize the first protective film 3A using sanitizer of the flexible pipe 4. In block S27, the motor driving module 102 drives the second motor roller 32 to draw the second protective film 3B to overlay on the surface of the touch screen 2. Referring to 4A, the first protective film 3A may be cleaned and sanitized by the sanitizer when the first motor roller 31 is scrolled, and the second protective film 3B is overlaid on the surface of the touch screen 2.

In block S28, the motor driving module 102 drives the second motor roller 32 to move along the surface of the second protective film 3B and sanitize the second protective film 3B using the sanitizer of the flexible pipe 4. In block S29, the motor driving module 102 drives the first motor roller 31 to draw the first protective film 3A to overlay on the surface of the touch screen 2. Referring to 4B, the second protective film 3B may be cleaned and sanitized by the sanitizer when the second motor roller 32 is scrolled, and the first protective film 3A is overlaid on the surface of the touch screen 2.

All of the processes described above may be embodied in, and fully automated via, functional code modules executed by one or more general purpose processors of the electronic devices. The code modules may be stored in any type of non-transitory readable medium or other storage device. Some or all of the methods may alternatively be embodied in specialized hardware. Depending on the embodiment, the non-transitory readable medium may be a hard disk drive, a compact disc, a digital video disc, a tape drive or other suitable storage medium.

Although certain disclosed embodiments of the present disclosure have been specifically described, the present disclosure is not to be construed as being limited thereto. Various changes or modifications may be made to the present disclosure without departing from the scope and spirit of the present disclosure.

What is claimed is:

1. An electronic device for performing a method for sanitizing a touch screen of the electronic device, the electronic device comprising:
   a first motor roller positioned on a left side of the touch screen;
   a second motor roller positioned on a right side of the touch screen; and
   one or more programs stored in a storage system comprising one or more programs and executable by at least one processor, the one or more programs comprising:
   a parameter setting module operable to set a time interval that determines how often to sanitize a protective film overlaid on a surface of the touch screen, the protective film being divided into a first protective film and a second protective film;
   a screen monitoring module operable to monitor whether the electronic device is in an idle state, count a time using a timer of the electronic device when the electronic device is in the idle state, and detect whether the first protective film or the second protective film is overlaid on the surface of the touch screen when the counted time is equal to the time interval; and
   a motor driving module operable to drive the first motor roller to move along a surface of the first protective film and sanitize the first protective film using a sanitizer, drive the second motor roller to draw the second protective film to overlay on the surface of the touch screen, drive the second motor roller to move along a surface of the second protective film and sanitize the second protective film using the sanitizer, and drive the first motor roller to draw the first protective film to overlay on the surface of the touch screen.

2. The electronic device according to claim 1, wherein the first motor roller connects to the second motor roller through a flexible pipe that is filled with the sanitizer.

3. The electronic device according to claim 1, wherein the first motor roller includes a first clasp that clasps on a left edge of the first protective film, and draws the first protective film into the first motor roller to be cleaned and sanitized using the sanitizer when the first motor roller is scrolled.

4. The electronic device according to claim 1, wherein the second motor roller includes a second clasp that clasps on a right edge of the second protective film, and draws the second protective film into the second motor roller to be cleaned and sanitized using the sanitizer when the second motor roller is scrolled.

5. The electronic device according to claim 1, wherein the electronic device comprises a universal serial bus (USB) port that is electronically connected to the first motor roller and the second motor roller.

6. The electronic device according to claim 1, wherein the protective film is a transparent film using a crystalline material without stickiness.

7. A method for sanitizing a touch screen of an electronic device, the method comprising:
  providing a first motor roller positioned on a left side of the touch screen, and providing a second motor roller positioned on a right side of the touch screen;
  setting a time interval that determines how often to sanitize a protective film overlaid on a surface of the touch screen, the protective film being divided into a first protective film and a second protective film;
  monitoring whether the electronic device is in an idle state;
  counting a time using a timer of the electronic device if the electronic device is in the idle state;
  detecting whether the first protective film or the second protective film is overlaid on the surface of the touch screen when the counted time is equal to the time interval; and
  upon the condition that the first protective film is overlaid on the surface of the touch screen, driving the first motor roller to move along a surface of the first protective film and sanitize the first protective film using a sanitizer, and driving the second motor roller to draw the second protective film to overlay on the surface of the touch screen; or
  upon the condition that the second protective film is overlaid on the surface of the touch screen, driving the second motor roller to move along a surface of the second protective film and sanitize the second protective film using the sanitizer, and driving the first motor roller to draw the first protective film to overlay on the surface of the touch screen.

8. The method according to claim 7, wherein the first motor roller connects to the second motor roller through a flexible pipe that is filled with the sanitizer.

9. The method according to claim 7, wherein the first motor roller includes a first clasp that clasps on a left edge of the first protective film, and draws the first protective film into the first motor roller to be cleaned and sanitized using the sanitizer when the first motor roller is scrolled.

10. The method according to claim 7, wherein the second motor roller includes a second clasp that clasps on a right edge of the second protective film, and draws the second protective film into the second motor roller to be cleaned and sanitized using the sanitizer when the second motor roller is scrolled.

11. The method according to claim 7, wherein the electronic device comprises a universal serial bus (USB) port that is electronically connected to the first motor roller and the second motor roller.

12. The method according to claim 7, wherein the protective film is a transparent film using a crystalline material without stickiness.

13. A non-transitory computer-readable medium having stored thereon instructions that, when executed by at least one processor of an electronic device, cause the processor to perform a method for a touch screen of the electronic device, the method comprising:
  installing a first motor roller on a left side of the touch screen, and installing a second motor roller on a right side of the touch screen;
  setting a time interval that determines how often to sanitize a protective film overlaid on a surface of the touch screen, the protective film being divided into a first protective film and a second protective film;
  monitoring whether the electronic device is in an idle state;
  counting a time using a timer of the electronic device if the electronic device is in the idle state;
  detecting whether the first protective film or the second protective film is overlaid on the surface of the touch screen when the counted time is equal to the time interval; and
  upon the condition that the first protective film is overlaid on the surface of the touch screen, driving the first motor roller to move along a surface of the first protective film and sanitize the first protective film using a sanitizer, and driving the second motor roller to draw the second protective film to overlay on the surface of the touch screen; or
  upon the condition that the second protective film is overlaid on the surface of the touch screen, driving the second motor roller to move along a surface of the second protective film and sanitize the second protective film using the sanitizer, and driving the first motor roller to draw the first protective film to overlay on the surface of the touch screen.

14. The non-transitory computer-readable medium according to claim 13, wherein the first motor roller connects to the second motor roller through a flexible pipe that is filled with the sanitizer.

15. The non-transitory computer-readable medium according to claim 13, wherein the first motor roller includes a first clasp that clasps on a left edge of the first protective film, and draws the first protective film into the first motor roller to be cleaned and sanitized using the sanitizer when the first motor roller is scrolled.

16. The non-transitory computer-readable medium according to claim 13, wherein the second motor roller includes a second clasp that clasps on a right edge of the second protective film, and draws the second protective film into the second motor roller to be cleaned and sanitized using the sanitizer when the second motor roller is scrolled.

17. The non-transitory computer-readable medium according to claim 13, wherein the electronic device comprises a universal serial bus (USB) port that is electronically connected to the first motor roller and the second motor roller.

18. The non-transitory computer-readable medium according to claim 13, wherein the protective film is a transparent film using a crystalline material without stickiness.

* * * * *